United States Patent [19]

Frenier et al.

[11] 3,969,414
[45] July 13, 1976

[54] NAPHTHYLMETHYL SULFONIUM COMPOUNDS

[75] Inventors: Wayne W. Frenier; William J. Settineri, both of Midland, Mich.

[73] Assignee: The Dow Chemical Company, Midland, Mich.

[22] Filed: Feb. 18, 1975

[21] Appl. No.: 550,401

Related U.S. Application Data

[63] Continuation-in-part of Ser. No. 350,295, April 11, 1973.

[52] U.S. Cl. .................. 260/607 B; 260/327 R; 260/327 TH; 252/395
[51] Int. Cl.² ........................... C07C 149/46
[58] Field of Search...... 260/607 B, 327 R, 327 TH; 252/395

[56] References Cited
UNITED STATES PATENTS
3,773,675  11/1973  Heiss ........................... 260/607 B

OTHER PUBLICATIONS

J. Chem. Soc. vol. 55, pp. 4747–4753, (1960).

*Primary Examiner*—Lewis Gotts
*Assistant Examiner*—D. R. Phillips
*Attorney, Agent, or Firm*—L. Wayne White

[57] ABSTRACT

Novel sulfonium compounds are described herein which correspond to the formula

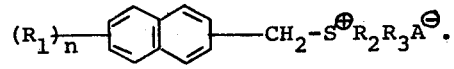

The sulfonium compounds are useful corrosion inhibitors in acidic cleaning solutions.

11 Claims, No Drawings

NAPHTHYLMETHYL SULFONIUM COMPOUNDS

CROSS-REFERENCE TO RELATED APPLICATIONS

This application is a continuation-in-part of our commonly owned U.S. patent application Ser. No. 350,295 filed on Apr. 11, 1973, which was entitled "Sulfonium Corrosion Inhibitors for Aqueous Acidic Cleaning Solutions". Disclosure of Ser. No. 350,295 is incorporated herein by reference.

SUMMARY OF THE INVENTION

We have discovered a novel class of sulfonium compounds which correspond to the general formula

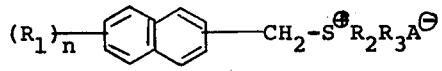

wherein $n$ is 1 or 2; each $R_1$ independently is hydrogen or a hydrocarbyl, hydrocarbyloxy or hydrocarbylthio group of from 1 to about 24 carbon atoms, or a hydrocarbyl group of from 1 to about 24 carbon atoms whose chain length is interrupted by an atom of oxygen or sulfur; $R_2$ is a hydrocarbyl radical of from 1 to about 24 carbon atoms, with the proviso that the total carbon content of $R_1$ and $R_2$ is from 7 to about 25 carbon atoms; $R_3$ is an alkyl radical of from 1 to 4 carbon atoms, allyl or a phenyl radical; or $R_2$ and $R_3$ are joined to form a 5- or 6-membered heterocyclic ring, with the proviso that the total aggregate carbon content of $R_1$, $R_2$ and $R_3$ is from 10 to about 25 carbon atoms; and $A^{\ominus}$ is a neutralizing anion.

The sulfonium compounds are useful corrosion inhibitors in acidic cleaning solutions and are surprisingly effective even in very low concentrations (e.g., from 2 to 4 millimoles/liter) and in the presence of ferric ions. Most acid corrosion inhibitors are ineffective in the presense of ferric ions.

DETAILED DESCRIPTION OF THE INVENTION

The instant class of compounds are typically prepared in the reaction illustrated below:

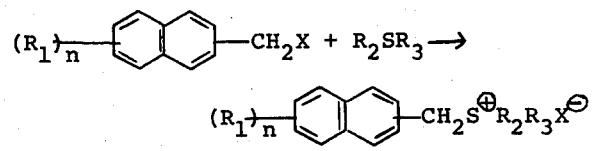

In this illustration, of course, X is halogen (e.g., chloro or bromo) and becomes the anion ($A^{\ominus}$) in the final product. The above reaction is normally conducted at a reaction temperature of from about 20° to about 55°C. in aqueous methanol or aqueous ethanol as the reaction medium. The sulfonium compounds are of course, water-soluble or dispersible and are also soluble in the above-mentioned reaction mediums. The corresponding sulfonium salts containing other anions are conveniently prepared by conventional ion-exchange techniques.

The classes of reactants used in the above reaction are, of course, known classes of compounds and thus require no further identification. The halomethylated naphthalenes are illustrated, for example, in U.S. Pat. Nos. 2,596,091 and 2,596,093. They are prepared by reacting naphthalene or an alkylated naphthalene with formaldehyde and hydrogen chloride or hydrogen bromide. The chloromethyl derivatives can also be prepared by reacting naphthalene or an alkylated naphthalene with chloromethyl methyl ether. These techniques are conventional preparative methods.

In the above generic formula for the instant compounds, $n$ is preferably 1; $R_1$ is preferably hydrogen or alkyl and is most preferably alkyl from 8 to about 18 carbon atoms; the ring position of the $R_1$ substituents is not critical but is preferably at least two ring carbons removed from the ring carbon bearing the —CH$_2$—S$^{\oplus}$R$_2$R$_3$A$^{\ominus}$ group; $R_2$ is preferably alkyl or allyl and is most preferably alkyl; $R_3$ is preferably alkyl or allyl and is most preferably alkyl; $A^{\ominus}$ is a compatible neutralizing anion and is preferably chloride, bromide, nitrate or acetate and is most preferably chloride.

The following example further illustrates the invention:

EXAMPLE 1

Chloromethylated dodecyl naphthalene (12.6 g) was reacted with dimethylsulfide (5 g) is 31 milliliters of methanol and enough water to bring the mixture to a "cloud point". The reaction mixture was stirred together at 25°C for 168 hours. The reaction mixture was washed with methylene chloride and warmed gently under reduced pressure to remove unreacted dimethyl sulfide and other volatiles. The desired product was thus obtained in the form of an emulsion in the residual water phase. Free chloride was titrated in an aliquot of the aqueous emulsion and indicated a successful displacement reaction. The half-wave potential of the compound was measured versus a saturated calomel electrode and measured −0.97 volts. The compound was an excellent inhibitor for the corrosion of mild steel in acidic cleaning solutions containing ferric ions (e.g., aqueous HCl or buffered aqueous ethylenediaminetetraacetic acid solutions containing from 0.1 to 0.3 percent ferric ions).

We claim:

1. A compound corresponding to the formula

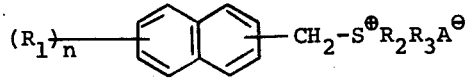

wherein $n$ is 1 or 2; each $R_1$ independently is a hydrocarbyl, hydrocarbyloxy or hydrocarbylthio group of from 1 to about 24 carbon atoms, or a hydrocarbyl group of from 1 to about 24 carbon atoms whose chain length is interrupted by an atom of oxygen or sulfur; $R_2$ is a hydrocarbyl radical of from 1 to about 24 carbon atoms, with the proviso that the total carbon content of $R_1$ and $R_2$ is from 7 to about 25 carbon atoms; $R_3$ is an alkyl radical of from 1 to 4 carbon atoms, allyl or a phenyl radical; and $A^{\ominus}$ is a neutralizing anion.

2. The compound defined by claim 1 wherein $n$ is 1; $R_1$ is alkyl; $R_2$ and $R_3$ are alkyl or allyl.

3. The compound defined by claim 2 wherein $R_2$ and $R_3$ are each alkyl.

4. The compound defined by claim 3 wherein $R_2$ and $R_3$ are each methyl.

5. The compound defined by claim 2 wherein $R_2$ and $R_3$ are each allyl.

6. The compound defined by claim 3 wherein $R_1$ is an alkyl radical of from 8 to 18 carbon atoms.

7. The compound defined by claim 6 wherein $R_1$ is dodecyl, $R_2$ and $R_3$ are each methyl, and $A^\ominus$ is chloride.

8. The compound defined by claim 1 wherein $R_1$ is an alkyl radical of from 8 to 18 carbon atoms.

9. The compound defined by claim 8 wherein $n$ is 1; $R_2$ and $R_3$ are alkyl or allyl.

10. The compound defined by claim 6 wherein $R_2$ and $R_3$ are each methyl.

11. The compound defined by claim 9 wherein $R_2$ and $R_3$ are each allyl.

* * * * *